United States Patent [19]

Nakano et al.

[11] Patent Number: 4,515,977

[45] Date of Patent: May 7, 1985

[54] PROCESS FOR PREPARING OPTICALLY ACTIVE [S]-2-ACETYL-7-(2-HYDROXY-3-ISO-PROPYLAMINOPROPOXY)BENZOFURAN AND SALTS THEREOF

[75] Inventors: Jun Nakano, Moriyama; Teruo Nakanishi, Kyoto; Kazuhiko Kimura, Otsu, all of Japan

[73] Assignee: Kaken Pharmaceutical Co., Ltd., Tokyo, Japan

[21] Appl. No.: 475,925

[22] Filed: Mar. 16, 1983

[30] Foreign Application Priority Data

Mar. 16, 1982 [JP] Japan .................................. 57-42145

[51] Int. Cl.³ .......................................... C07D 307/86
[52] U.S. Cl. .................................................. 549/468
[58] Field of Search ............................................ 549/468

[56] References Cited

FOREIGN PATENT DOCUMENTS 49-43960  4/1974  Japan ................................... 549/468

OTHER PUBLICATIONS

Nakano et al., Heterocycles, vol. 20, pp. 1975–1978, (1983).
Bittner et al., Chemistry and Industry, p. 281, (1975).

*Primary Examiner*—Henry R. Jiles
*Assistant Examiner*—Bernard I. Dentz
*Attorney, Agent, or Firm*—Armstrong, Nikaido, Marmelstein & Kubovcik

[57] ABSTRACT

[S]-(+)-2-acetyl-7-(2,3-epoxypropoxy)benzofuran (SEBF) is prepared by subjecting 2-acetyl-7-hydroxybenzofuran and [R]-glycidol to dehydration condensation in an inert organic solvent in the presence of triphenylphosphine and a dialkyl azodicarboxylate. The [S]-(+)-2-acetyl-7-(2,3-epoxypropoxy)benzofuran can be easily converted into [S]-2-acetyl-7-(2-hydroxy-3-isopropylaminopropoxy)benzofuran ([S]-befunolol) or salts thereof which are useful as a β-adrenergic blocking agent, by reacting it with isopropylamine.

2 Claims, No Drawings

PROCESS FOR PREPARING OPTICALLY ACTIVE [S]-2-ACETYL-7-(2-HYDROXY-3-ISO-PROPYLAMINOPROPOXY)BENZOFURAN AND SALTS THEREOF

BACKGROUND OF THE INVENTION

The present invention relates to a novel process for preparing [S]-2-acetyl-7-(2-hydroxy-3-isopropylaminopropoxy)benzofuran (hereinafter referred to as "[S]-befunolol") or salts thereof, more particularly to a process for preparing the [S]-befunolol or salts thereof through optically active [S]-(+)-2-acetyl-7-(2,3-epoxypropoxy)benzofuran (hereinafter referred to as "SEBF").

SEBF is important as an intermediate for synthesis of various optically active organic compounds, particularly as an intermediate for synthesis of [S]-(−)-befunolol hydrochloride and the other salts thereof which are very useful as a β-adrenergic blocking agent (hereinafter referred to as "β-blocker") in prevention and treatment of heart disease such as arrhythmia or angina pectoris and hypertension and treatment of glaucoma as disclosed in Japanese Examined Patent Publication No. 20,063/1975.

Most β-blockers have a peculiar moiety represented by the following formula:

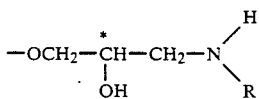

and accordingly optical isomers based on the symmetric carbon atom (carbon atom with star mark) are present. In many β-blockers hitherto known, it is known that an optically active compound having [S]-configuration (hereinafter referred to as "S-form") has in general a higher pharmacological activity than its mirror-image isomer (hereinafter referred to as "R-form") and the racemic compounds as, for instance, reported in J. Med. Chem., 11, 1118(1968). Befunolol hydrochloride is not an exception thereto, and for instance, it is admitted that in a test examining antagonism against heart contraction enhancement of isoproterenol in dogs, the S-form has about 40 times higher activity than the R-form. Therefore, it has been demanded to develop a process for preparing [S]-befunolol selectively and easily in high yields. In such a process, SEBF is one of the useful and practical intermediates.

As representative processes for obtaining [S]-β-blockers, there are well known (1) an optical resolution process and (2) a process in which naturally abundant [D]-mannitol is used as a chiral source and the asymmetric carbon atom thereof is introduced into a desired compound. The optical resolution process (1) has the drawback that a resolving reagent is difficult to obtain. Therefore, in case of intending industrial preparation, the process (2) utilizing [D]-mannitol is rather superior and many studies thereof have been made. The present inventors have also made a study in line with the same object on a process capable of synthesizing SEBF into which the asymmetric carbon atom of [D]-mannitol is introduced by a novel method.

The prior art in the field of this invention teaches the reaction of various optically active reacting reagents obtained from [D]-mannitol, e.g. [R]- or [S]-epichlorohydrin (cf. Japanese Examined Patent Publication No. 43775/1971), [R]- or [S]-mesyloxymethyloxirane [cf. J. Am. Chem. Soc., 101, 3666(1979)], and [R]- or [S]-3-tosyloxy-1,2-propanediolacetonide (cf. Japanese Unexamined Patent Publication No. 77331/1975), with a phenolic compound under a basic condition. That is, these prior art teachings all utilize nucleophilic substitution of phenoxide anion (ArO−) produced during the reaction for the leaving group (halogen atom, mesyloxy group, p-toluenesulfonyloxy group) in the reacting reagents. However, if such a nucleophilic substitution reaction is applied to the preparation of SEBF, the desired substitution product is hard to obtain in high yields owing to the considerably basic condition utilized.

In the preparation of 2-acetyl-7-(2,3-epoxypropoxy)-benzofuran racemic compounds, there has been adopted a process in which 2-acetyl-7-hydroxybenzofuran of the formula:

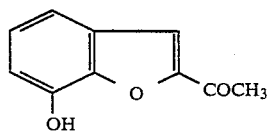

is reacted with a large excess of (±)-epichlorohydrin by employing piperidine hydrochloride which is a weak basic compound, as a base catalyst, as known from Japanese Examined Patent Publication No. 20063/1975. However, application of this process to the preparation of SEBF requires a large quantity of an expensive optically active compound, e.g. optically active epichlorohydrin, and accordingly has little practical value. Therefore, in the preparation of SEBF, it is ideal to utilize an entirely different process to replace conventional processes utilizing the nucleophilic substitution reaction. For instance, a process could be used in which the reaction is able to proceed under such a moderate condition that the reaction system is maintained in the vicinity of neutral condition throughout the reaction.

It is an object of the present invention to provide a process for preparing optically active [S]-befunolol and pharmaceutically acceptable salts thereof in high yields.

Another object of the invention is to provide a process for preparing an optically active [S]-2-acetyl-7-(2,3-epoxypropoxy)benzofuran (SEBF) which can be easily converted into [S]-befunolol.

These and other objects of the present invention will become apparent from the description hereinafter.

SUMMARY OF THE INVENTION

In accordance with the present invention, there is provided a process for preparing [S]-2-acetyl-7-(2,3-epoxypropoxy)benzofuran (SEBF) of the following formula:

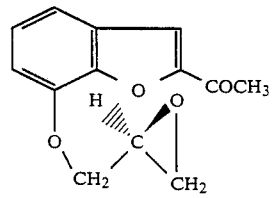

which comprises subjecting 2-acetyl-7-hydroxybenzofuran of the formula (I):

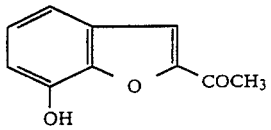

and [R]-glycidol of the formula (II):

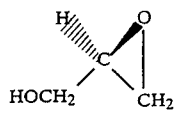

to redox dehydration condensation in an inert organic solvent in the presence of triphenylphosphine and a dialkyl azodicarboxylate.

The [S]-2-acetyl-7-(2,3-epoxypropoxy)-benzofuran (SEBF) can be readily converted into [S]-2-acetyl-7-(2-hydroxy-3-isopropylaminopropoxy)benzofuran ([S]-befunolol) or its pharmaceutically acceptable salts by reacting with isopropylamine.

DETAILED DESCRIPTION

2-Acetyl-7-hydroxybenzofuran (I) used in the process of the present invention can be easily obtained from o-vanillin. Also, [R]-glycidol (II) used in the process of the invention can be obtained from [D]-mannitol through a relatively short procedure.

Although the amounts of the reactants are not particularly limited, [R]-glycidol is usually employed in an amount of about 1 to 1.5 equivalents per equivalent of the compound (I). Triphenylphosphine of the formula:

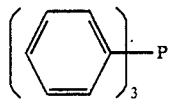

and a dialkyl azodicarboxylate of the general formula:

$$RO_2CN=NCO_2R$$

wherein

R is an alkyl group, preferably having 1 to 4 carbon atoms, are employed respectively in amounts equal to the [R]-glycidol used, within the range of about 1 to 1.5 equivalents per equivalent of the compound (I).

The reaction for producing SEBF in the process of the invention is represented as follows:

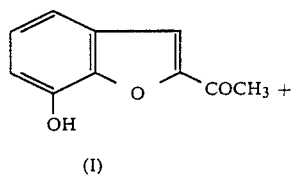

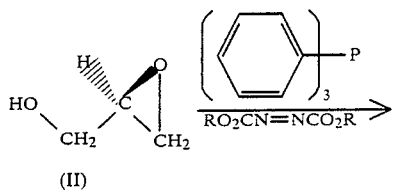

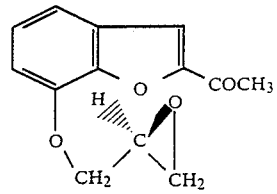

The above reaction is usually carried out under an atmosphere of an inert gas such as nitrogen gas or argon gas in a dry inert organic solvent such as tetrahydrofuran. chloroform or benzene. The order of introducing the reaction reagents is not particularly limited, but preferably, the reaction is carried out in a manner such that the compound (I), [R]-glycidol (II) and triphenylphosphine are dissolved in an organic solvent in that order and a dialkyl azodicarboxylate is then gradually added dropwise to the solution with agitation. The reaction temperature is selected from $-20°$ to $50°$ C., preferably $0°$ to $20°$ C. The reaction is completed by, after the dropwise addition of the dialkyl diazodicarboxylate, conducting the agitation for about 1 to 5 hours within the above temperature range.

According to the process of the invention, the reaction system is maintained in the vicinity of neutral condition throughout the reaction, and accordingly the side reaction or decomposition of the reactants and the product is insignificant and SEBF can be obtained in high yields. Also, since the redox dehydration reaction proceeds in a regioselective manner at the carbon having a primary hydroxyl group of [R]-glycidol, the apprehensive racemization is small and SEBF having a high optical purity can be obtained.

[S]-Befunolol can be easily obtained by reacting SEBF with isopropylamine. The reaction is usually carried out in an organic solvent such as methanol and ethanol at a temperature of $30°$ to $80°$ C. for 0.1 to 2 hours. For instance, SEBF is dissolved in ethanol, and after adding isopropylamine to the solution, it was heated under reflux for 30 minutes to 1 hour. [S]-Befunolol can be easily converted into its pharmaceutically acceptable acid salts in a conventional manner, for instance, by treating it with an acid such as hydrochloric acid, sulfuric acid, nitric acid, succinic acid, tartaric acid, maleic acid or citric acid. The treatment with an acid may be conducted in a suitable solvent such as methanol, ethanol or a chloroform-ethyl acetate mixed solvent. The acid salts are recovered in a usual manner, and if necessary, they are purified by crystallization from a suitable solvent such as ethanol, isopropanol or a chloroform-ethyl acetate mixed solvent.

The present invention is more specifically described and explained by means of the following Reference Example and Examples. The Reference Example is to illustrate the preparation of [R]-glycidol which is used as a starting material in the process of the invention. It is to be understood that the present invention is not limited to the Examples, and various changes and modifications may be made in the invention without departing from the spirit and scope thereof.

REFERENCE EXAMPLE 1

[Preparation of [R]-glycidol]

In a mixture of 100 ml. of dry methanol and 50 ml. of dry ether was dissolved 62.7 g. of [R]-3-p-tosyloxy-1,2-propanediol prepared from [D]-mannitol according to a usual method [e.g. as disclosed in J. Org. Chem., 43, 4877(1978)]. To the solution was gradually added 5.4 g. of metallic sodium with ice cooling, and they were agitated for 1 hour with ice cooling. After the completion of the reaction, the reaction mixture was concentrated under reduced pressure. To the residue was added 200 ml. of ether, and the solution was filtered to remove insoluble materials. The filtrate was concentrated under reduced pressure, 100 ml. of ether was added to the residue and insoluble materials were removed by filtration. Further, the filtrate was concentrated under reduced pressure, 100 ml. of chloroform was added to the residue and insoluble materials were removed by filtration. The filtrate was concentrated under reduced pressure to give 14.4 g. of [R]-glycidol as a colorless oily material. The yield was 89%. The obtained [R]-glycidol was further purified by vacuum distillation, and was subjected to analysis. The analytical results of the product are as follows:

Boiling point: 70° C./15 mmHg.

$[\alpha]_D^{24}$: +16.5° (C 5.88, CHCl$_3$).

Analysis for $C_3H_6O_2$ (molecular weight: 74.03): Calcd. (%): C, 48.65; H, 8.11. Found: (%): C, 48.60; H, 7.90.

NMR spectrum (solvent: CDCl$_3$, internal standard: TMS): δ values 2.75 (2H, m), 3.16 (1H, m), 3.55 (1H, dd), 3.95 (1H, dd) p.p.m.

EXAMPLE 1

[Preparation of SEBF]

In 150 ml. of dry tetrahydrofuran were dissolved 17.6 g. of 2-acetyl-7-hydroxybenzofuran, 9.6 g. of [R]-glycidol and 34.1 g. of triphenylphosphine. To the solution was added dropwise 22.6 g. of diethyl azodicarboxylate under a nitrogen atmosphere over about 30 minutes, while maintaining the temperature below 20° C. with ice cooling. After the completion of the dropwise addition, the reaction was completed by agitating the mixture at a temperature of 10° to 20° C. for 3 hours. The solvent was then distilled away under reduced pressure, and 100 ml. of diethyl ether was added to the residue. The solution was cooled and the resulting precipitate was separated by filtration. The filtrate was concentrated under reduced pressure, and the obtained residue was purified by silica gel column chromatography (eluent: methylene chloride/n-hexane/ether = 3/3/1) to give 18.5 g. of the pure desired compound (yield: 80%). The product was further purified by recrystallization from a mixed solvent of benzene and n/hexane (1:5). The analytical results of the so purified SEBF are as follows:

Melting point: 74.6° C.

Analysis for $C_{13}H_{12}O_4$ (molecular weight: 232.13): Calcd. (%): C, 67.24; H 5.17. Found (%): C, 67.20; H 5.19.

$[\alpha]_D^{24}$: +27.6° (C 1.00, MeOH).

Mass spectrum (M/e): 2.32 (M+), 202, 189, 176, 161.

NMR spectrum (solvent: CDCl$_3$, internal standard: TMS): δ values 2.59 (3H, s), 2.78–3.02 (2H, m), 3.36–3.58 (1H, m), 4.11–4.28 (1H, dd), 4.45–4.62 (1H, dd), 7.03–7.43 (4H, m) p.p.m.

[Preparation of [S]-(−)-befunolol hydrochloride]

In 150 ml. of ethanol was dissolved 27.8 g. of SEBF, and thereto was added 30 ml. of isopropylamine. The mixture was then heated under reflux for 40 minutes. After the completion of the reaction, ethanol and isopropylamine were dissolved away under reduced pressure, and the resulting residue (crude [S]-befunolol) was dissolved in 150 ml. of concentrated hydrochloric acid with ice cooling. After the addition of hydrochloric acid, the mixture was further agitated for 10 minutes with ice cooling. Ethanol was removed with water as an azeotropic mixture by distillation under reduced pressure. The residue was crystallized from isopropyl alcohol to give crude crystals. The obtained crude crystals were further subjected to recrystallization from 100 ml. of isopropyl alcohol to give 29.4 g. of [S]-(−)-befunolol hydrochloride (yield: 75.0%). The analytical results are as follows:

Melting point: 151° to 152° C.

Analysis for $C_{16}H_{21}NO_4 \cdot HCl$ (molecular weight: 327.81): Calcd. (%): C, 58.62, H, 6.76; N, 4.27; Cl, 10.81. Found (%): C, 58.33; H, 6.57; N, 4.04; Cl, 11.08.

$[\alpha]_D^{24}$: −15.5° (C 1.00, MeOH).

Infrared absorption spectrum ($\nu_{max}^{KBr}$ cm.$^{-1}$): 3375, 1680.

NMR spectrum (solvent: D$_2$O, internal standard: TMS): δ values 1.55 (6H, d), 2.52 (3H, s), 3.50 (2H, d), 3.65 (1H, m), 4.25 (2H, d), 4.45 (1H, m), 6.9–7.3 (3H, m), 7.45 (1H, s) p.p.m.

Mass spectrum (M/e): 291, 276, 247, 176, 161, 102, 72.

EXAMPLE 2

[Preparation of SEBF]

SEBF was prepared in the same manner as in Example 1 except that 26.3 g. of diisopropyl azodicarboxylate was employed instead of diethyl dicarboxylate (yield of SEBF: 17.4 g., 75%). The analytical results of the obtained SEBF are as follows:

Melting point: 74.5° C.

Analysis for $C_{13}H_{12}O_4$ (molecular weight: 232.13): Calcd. (%): C, 67.24; H, 5.17. Found (%): C, 67.30; H, 5.15.

$[\alpha]_D^{24}$: +27.6° (C 1.00, MeOH).

[Preparation of [S]-(−)-befunolol succinate]

[S]-Befunolol was then prepared in the same manner as in Example 1 by employing the thus obtained SEBF. In a mixed solvent of 250 ml. of ethyl acetate and 125 ml. of chloroform was dissolved 10 g. of the obtained [S]-befunolol with heating, and thereto was added a solution of 2.1 g. of succinic acid dissolved in 24 ml. of ethanol. The solution was filtered and allowed to stand at room temperature to give 11 g. of crude crystals. The crude crystals were further subjected to recrystallization from 450 ml. of a ethyl acetatechloroform mixed solvent (2:1 by volume) to give 10 g. of [S]-(−)-befunolol succinate. The analytical results are as follows:

Melting point: 140° to 141° C.

Analysis for $C_{16}H_{21}NO_4 \cdot \frac{1}{2}C_4H_6O_4$: Calcd. (%): C, 61.69; H, 6.92; N, 4.00. Found (%): C, 61.46; H, 6.86; N, 3.85.

$[\alpha]_D^{24}$: −10.2° (C 1.00, MeOH).

NMR spectrum (solvent: DMSO-d₆, internal standard: TMS): δ values 1.12 (6H, d) 2.25 (2H, s) 2.50 (3H, s), 3.05–2.73 (3H, m), 4.06 (3H, br.s), 6.97–7.28 (3H, m), 7.70 (1H, s) p.p.m.

Infrared absorption spectrum ($\nu_{max}^{nujol}$ cm.$^{-1}$): 3370, 1680.

Mass spectrum (M/e): 291, 276, 247, 176, 161, 72.

What we claim is:

1. A process for preparing [S]-2-acetyl-7-(2,3-epoxypropoxy)benzofuran of the following formula:

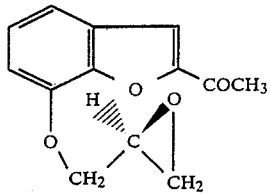

which comprises subjecting 2-acetyl-7-hydroxybenzofuran of the formula (I):

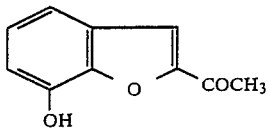
(I)

and [R]-glycidol of the formula (II):

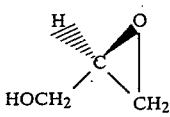
(II)

to redox dehydration condensation in an inert organic solvent in the presence of triphenylphosphine and a dialkyl azodicarboxylate.

2. A process for preparing [S]-2-acetyl-7-(2-hydroxy-3-isopropylaminopropoxy)benzofuran or pharmaceutically acceptable salts thereof which comprises subjecting 2-acetyl-7-hydroxybenzofuran of the formula

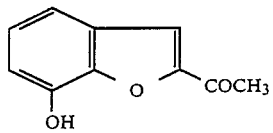
(I)

and [R]-glycidol of the formula (II):

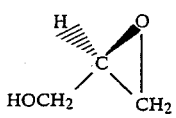
(II)

to redox dehydration condensation in an inert organic solvent in the presence of triphenylphosphine and a dialkyl azodicarboxylate to produce [S]-2-acetyl-7-(2,3-epoxypropoxy)benzofuran of the formula (III):

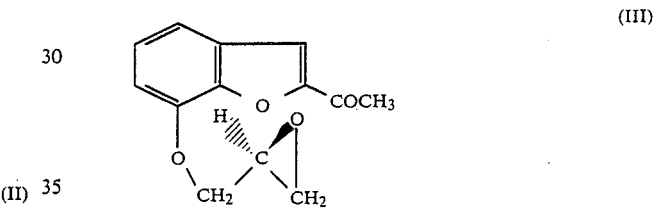
(III)

and reacting the resulting [S]-2-acetyl-7-(2,3-epoxypropoxy)benzofuran (III) with isopropylamine.

* * * * *

UNITED STATES PATENT AND TRADEMARK OFFICE
CERTIFICATE OF CORRECTION

PATENT NO. : 4,515,977

DATED : May 7, 1985

INVENTOR(S) : JUN NAKANO ET AL

It is certified that error appears in the above-identified patent and that said Letters Patent is hereby corrected as shown below:

Column 1, line 34, change "symmetric" to --- asymmetric ---.

Column 3, line 49, change "$RO_2CN\ NCO_2R$" to --- $RO_2CN=NCO_2R$ ---.

Column 2, line 56, change "[S]-2-acetyl" to --- [S]-(+)-2-acetyl ---.

Column 3, line 22, change "[S]-2-acetyl" to --- [S]-(+)-2-acetyl ---.

Column 7, line 10, change "[S]-2-acetyl" to --- [S]-(+)-2-acetyl ---.

UNITED STATES PATENT AND TRADEMARK OFFICE
CERTIFICATE OF CORRECTION

PATENT NO. : 4,515,977

DATED : May 7, 1985

INVENTOR(S) : JUN NAKANO ET AL

It is certified that error appears in the above-identified patent and that said Letters Patent is hereby corrected as shown below:

Column 8, line 25, change "[S]-2-acetyl" to --- [S]-(+)-2-acetyl ---.

Column 8, line 38, change "[S]-2-acetyl" to --- [S]-(+)-2-acetyl ---.

Signed and Sealed this

Eighteenth Day of March 1986

[SEAL]

Attest:

Attesting Officer

DONALD J. QUIGG

Commissioner of Patents and Trademarks